United States Patent
Kawagishi et al.

(10) Patent No.: US 8,518,859 B2
(45) Date of Patent: Aug. 27, 2013

(54) METHOD FOR INCREASING YIELD OF STAPLE FOOD CROP

(75) Inventors: Hirokazu Kawagishi, Shizuoka (JP); Akio Morita, Shizuoka (JP); Jae-Hoon Choi, Shizuoka (JP)

(73) Assignee: National University Corporation Shizuoka University, Shizuoka-shi (JP)

( * ) Notice: Subject to any disclaimer, the term of this patent is extended or adjusted under 35 U.S.C. 154(b) by 66 days.

(21) Appl. No.: 13/386,607

(22) PCT Filed: Jul. 22, 2010

(86) PCT No.: PCT/JP2010/062351
§ 371 (c)(1),
(2), (4) Date: Feb. 2, 2012

(87) PCT Pub. No.: WO2011/010695
PCT Pub. Date: Jan. 27, 2011

(65) Prior Publication Data
US 2012/0122690 A1    May 17, 2012

(30) Foreign Application Priority Data

Jul. 24, 2009 (JP) ................................ 2009-173724
Nov. 25, 2009 (JP) ................................ 2009-267916

(51) Int. Cl.
*A01N 43/46* (2006.01)

(52) U.S. Cl.
USPC ....................................................... 504/228

(58) Field of Classification Search
None
See application file for complete search history.

(56) References Cited

U.S. PATENT DOCUMENTS

| 4,350,520 A * | 9/1982 | Beck et al. ................ 504/279 |
| 4,808,213 A | 2/1989 | Schmierer et al. |
| 2006/0030490 A1 | 2/2006 | Hayashi et al. |
| 2006/0123507 A1 | 6/2006 | Ashikari et al. |
| 2008/0229445 A1 | 9/2008 | Frankard et al. |

FOREIGN PATENT DOCUMENTS

| EP | 0269238 A1 | 6/1988 |
| JP | 56092801 A | 7/1981 |
| JP | 63068570 A | 3/1988 |
| JP | 63104965 A | 5/1988 |
| JP | 04210680 A | 7/1992 |
| JP | 09000071 A | 1/1997 |
| JP | 2000038304 A | 2/2000 |
| JP | 2006045144 A | 2/2006 |
| JP | 2007515167 A | 6/2007 |
| JP | 2009001558 A | 1/2009 |
| JP | 4462566 | 5/2010 |

OTHER PUBLICATIONS

Cavender et al., J Agric Food Chem 36: 1076 (1988).*
Nitsch et al., "Auxin-Dependent Growth of Excised Helianthus Tuberosus Tissues II. Organic Nitrogenous Compounds," *Am J Botany*, 44:555-564 (1957).
International Search Report for PCT/2010/062351 dated Aug. 31, 2010.

* cited by examiner

*Primary Examiner* — James H Alstrum Acevedo
*Assistant Examiner* — Thor Nielsen
(74) *Attorney, Agent, or Firm* — Marshall, Gerstein & Borun LLP

(57) ABSTRACT

Provided is a method of increasing a yield of a staple food crop which comprises bringing a compound represented by the following Formula (I) into contact with a plant body, excluding seeds, of a staple food crop to be cultured. The staple food crop is preferably a cereal crop, a tuber crop or the like. In the following Formula (I), $R^1$ and $R^2$ each independently represent a hydrogen atom or a monovalent substituent, or $R^1$ and $R^2$ are bound together to form an azo group; and $R^3$ represents a hydrogen atom or a monovalent substituent.

10 Claims, No Drawings

METHOD FOR INCREASING YIELD OF STAPLE FOOD CROP

TECHNICAL FIELD

The present invention relates to a method of increasing the yield of a staple food crop.

BACKGROUND ART

As a chemical substance which regulates plant growth, so-called plant hormones are known. Generally, a plant hormone is a chemical substance which derives from a plant itself and regulates growth, differentiation, or the like, of a plant in trace amounts. In addition, a variety of chemical substances which do not derive from a plant per se but regulate plant growth are also known.

For example, 2-azahypoxanthine is a 2-aza-substituted hypoxanthine having a purine skeleton, which is known not only as a degradation product of dacarbazine (DTIC) which is an anticancer agent, but is also known to contribute to improvement of the germination ratio and shoot elongation in seeds of bentgrass and rice, as well as root elongation, mass increase and the like in lettuce (for example, see Japanese Patent Application Laid-Open (JP-A) No. 2009-1558).

Meanwhile, from the standpoint of agricultural policy, it is important to facilitate the growth of staple food crops, such as cereal crops including rice and maize and tuber crops, to increase the yield per unit area. In order to increase the yield of staple food crops, improvements have been made in fertilizers having high nutritional value; however, the adverse effects associated with the use of such fertilizers in large amounts have also been viewed as problematic.

From such standpoints as well, various plant growth regulators have been used, and for example, as an agent for increasing the yield of potato, $C_{12}$-$C_{24}$ monohydric alcohols such as stearyl alcohol (for example, see Japanese Patent Application Laid-Open (JP-A) No. 2006-45144), triazole-based compounds (for example, see Japanese Patent Application Laid-Open (JP-A) No. 9-71) and the like are known.

Further, it has also been attempted to increase the yield by breed improvement and a transgenic rice is also known into which the cyclin A gene and the like are introduced in order to attain an increase in the seed mass, number of filled seeds, number of seeds, seed size, harvest index and thousand-kernel weight, as well as modification of the seed composition (for example, see Japanese Unexamined Patent Application Publication (Translated PCT Patent Application) No. 2007-515167 and Japanese Patent No. 4462566).

DISCLOSURE OF THE INVENTION

Problems to be Solved by the Invention

However, so-called transgenic plants into which a gene is introduced are still not considered to be widely or easily accepted in the field of agricultural products, nor are they considered satisfactory from the standpoint of trait stability. In addition, there are concerns regarding synthetic plant growth regulators since they may adversely affect the soil since they do not derive from a natural product.

Therefore, an object of the present invention is to provide a method of increasing the yield of a staple food crop using a naturally-occurring compound, by which the yield of a staple food crop can be simply increased.

Means for Solving the Problems

The present invention is as follows.

[1] A method of increasing the yield of a staple food crop, the method comprising bringing a compound represented by the following Formula (I) into contact with a plant body, excluding seeds, of a staple food crop to be cultured.

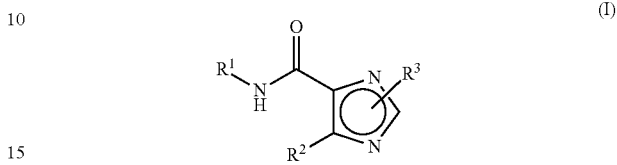

In Formula (I), $R^1$ and $R^2$ each independently represent a hydrogen atom or a monovalent substituent, or $R^1$ and $R^2$ are bound together to form an azo group; and $R^3$ represents a hydrogen atom or a monovalent substituent.

[2] The method of increasing the yield of a staple food crop according to [1], wherein the staple food crop is a cereal crop or a tuber crop.

[3] The method of increasing the yield of a staple food crop according to [1] or [2], the method comprising bringing the compound represented by Formula (I) into contact with a plant body of a Poaceae plant to be cultured and performing soil culture.

[4] The method of increasing the yield of a staple food crop according to [1] or [2], the method comprising bringing the compound represented by Formula (I) into contact with a plant body of a Poaceae plant to be cultured and performing hydroponic culture.

[5] The method of increasing the yield of a staple food crop according to [1] or [2], the method comprising bringing the compound represented by Formula (I) into contact with a plant body of a tuber crop to be cultured and performing soil culture, the tuber crop belonging to the family Solanaceae, Convolvulaceae, Asteraceae, Araceae, Dioscoreaceae or Euphorbiaceae.

Effects of the Invention

According to the present invention, a method of increasing the yield of a staple food crop, by which the yield of a staple food crop can be simply increased using a naturally-occurring compound, can be provided.

BEST MODE FOR CARRYING OUT THE INVENTION

The method of increasing the yield of a staple food crop according to the present invention includes bringing a compound represented by the following Formula (I) into contact with a plant body, excluding seeds, of a staple food crop plant to be cultured.

In the present invention, by bringing a compound represented by the following Formula (I) into contact with a plant body of a staple food crop plant to be cultured, the mass per plant of the staple food crop is increased. Consequently, the yield of the staple food crop increases as compared to a case where a compound represented by the following Formula (I) is not used.

In the present invention, an increase in the yield per plant of the staple food crop is believed to occur independently of an improvement in the seed germination ratio and an increase in the crop root elongation and the volume of the whole crop plant, and the increase in the yield per plant of the staple food crop refers to an increase in the yield as a staple food crop, that is, an increase in the edible parts, not the whole plant body.

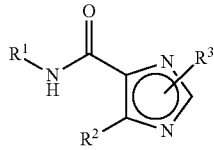
(I)

In Formula (I), $R^1$ and $R^2$ each independently represent a hydrogen atom or a monovalent substituent, or $R^1$ and $R^2$ are bound together to form an azo group; and $R^3$ represents a hydrogen atom or a monovalent substituent.

That is, the compound represented by Formula (I) is a 2-azahypoxanthine derivative represented by the following Chemical Formula (Ia) or an imidazole-4-carboxamide derivative represented by the following Chemical Formula (Ib).

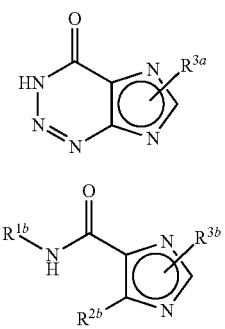
(Ia)

(Ib)

In Formula (Ia), $R^{3a}$ represents a hydrogen atom or a monovalent substituent. Further, in Formula (Ib), $R^{1b}$, $R^{2b}$ and $R^{3b}$ each independently represent a hydrogen atom or a monovalent substituent.

In the 2-azahypoxanthine derivative represented by Formula (Ia), $R^{3a}$ represents a hydrogen atom or a monovalent substituent. Examples of the monovalent substituent include a halogen atom, an alkyl group, an alkenyl group, an alkynyl group, an aryl group, a hydroxy group, an alkoxy group, an aryloxy group, an alkylthio group, an arylthio group, an amino group, an alkylamino group, an arylamino group, an acyl group, an acylamino group, an alkoxycarbonylamino group and an ureido group. In addition, if possible, these monovalent substituents may further have a substituent, and examples of the substituent include the same ones as those exemplified for the monovalent substituent.

From the standpoint of increasing the yield of the staple food crop, $R^{3a}$ is preferably a hydrogen atom, a halogen atom or an alkyl group, more preferably a hydrogen atom or an alkyl group, still more preferably a hydrogen atom.

Further, the alkyl group is preferably a $C_1$-$C_{10}$ alkyl group, more preferably a $C_1$-$C_8$ alkyl group having a substituent. Examples of the substituent in the above-described alkyl group include an amino group, an alkoxycarbonylamino group, a hydroxy group and an acyloxy group.

Further, in Formula (Ia), the substitution position of $R^{3a}$ is not particularly restricted as long as it is substitutable, and the substitution may be at a nitrogen atom or at a carbon atom.

Specific examples of the 2-azahypoxanthine derivative represented by Formula (Ia) include the following compounds; however, the present invention is not restricted by these compounds.

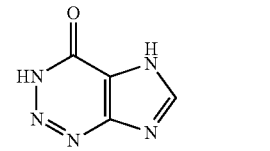

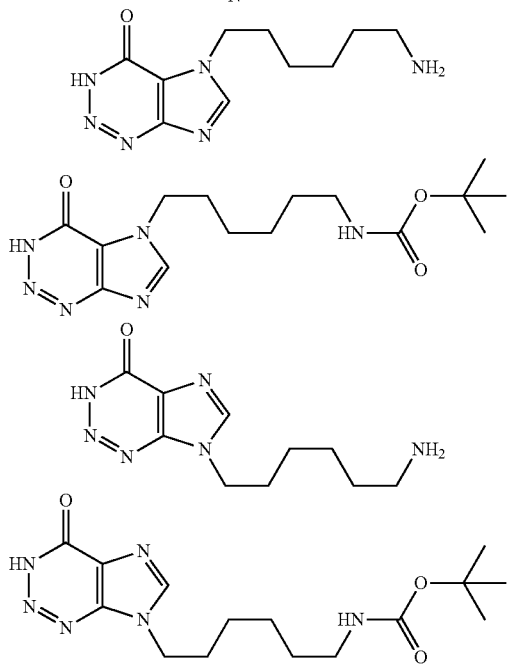

Among the 2-azahypoxanthine derivatives represented by Formula (Ia), 2-azahypoxanthine in which $R^{3a}$ is a hydrogen atom (hereinafter, may be referred to as "AHX") is a compound including tautomers represented by the following Chemical Formula. The AHX is a naturally-occurring compound known to be produced by, for example, a causative fungus of the fairy-ring phenomenon, which is a phenomenon in which a part of turfgrass exhibits greater growth in a circular pattern as compared to the surrounding area.

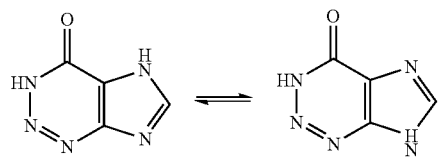 [SMILES: O=c1[nH]nnc2nc[nH]c12 ; O=c1[nH]nnc2[nH]cnc12]

The AHX may be isolated and purified from a culture medium of a causative fungus of the fairy-ring phenomenon by, for example, a conventionally-used method such as extraction or chromatography. Examples of the causative fungus include *Lepista sordida*.

In addition, the AHX may also be chemically synthesized by, for example, diazotizing 5-aminoimidazole-4-carboxamide and then cyclizing the resultant in accordance with the method described in Magn. Reson. Chem., 40, 300-302 (2002) or the like.

Further, a 2-azahypoxanthine derivative in which $R^{3a}$ is other than a hydrogen atom in Formula (Ia) can be synthesized by a conventionally-used method, for example, using the above-described AHX as a starting material. Specifically, for example, a compound in which $R^{3a}$ is an alkyl group can be synthesized by allowing a halogenated alkyl to react with the AHX.

In the imidazole-4-carboxamide derivative represented by Formula (Ib), $R^{1b}$, $R^{2b}$ and $R^{3b}$ each independently represent a hydrogen atom or a monovalent substituent. Examples of the monovalent substituent include a halogen atom, an alkyl group, an alkenyl group, an alkynyl group, an aryl group, a hydroxy group, an alkoxy group, an aryloxy group, an alkylthio group, an arylthio group, an amino group, an alkylamino group, an arylamino group, an acyl group, an acylamino group, an alkoxycarbonylamino group and an ureido group. In addition, if possible, these monovalent substituents may further have a substituent, and examples of the substituent include the same ones as those exemplified for the above-described monovalent substituent.

The alkyl group is preferably a $C_1$-$C_{10}$ alkyl group, more preferably a $C_1$-$C_8$ alkyl group, still more preferably a $C_1$-$C_6$ alkyl group, and specific examples thereof include methyl, ethyl, propyl, isopropyl, cyclopropyl, butyl, isobutyl, t-butyl, hexyl and cyclohexyl. In addition, the alkyl group may further have a substituent, and specific examples of such alkyl group include chloromethyl, chloroethyl, fluoromethyl, trifluoromethyl, hydroxymethyl, benzyl and phenylethyl.

As the alkenyl group, a $C_2$-$C_6$ alkenyl group is preferred, and specific examples thereof include vinyl, allyl and butenyl.

As the alkynyl group, a $C_2$-$C_6$ alkynyl group is preferred, and specific examples thereof include ethinyl and propynyl.

As the aryl group, a $C_6$-$C_{10}$ aryl group is preferred, and specific examples thereof include phenyl and naphthyl.

Examples of alkyl moiety in the alkoxy group, alkylthio group, alkylamino group, acyl group, acylamino group and alkoxycarbonylamino group include the same ones as those exemplified for the above-described alkyl group. Further, examples of aryl moiety in the aryloxy group, arylthio group and arylamino group include the same ones as those exemplified for the above-described aryl group.

Moreover, the ureido group may be either non-substituted one or an ureido group substituted with the above-described alkyl group or aryl group.

In the present invention, from the standpoint of increasing the yield of the staple food crop, the above-described $R^{1b}$, $R^{2b}$ and $R^{3b}$ each independently are preferably a group selected from a hydrogen atom, a halogen atom, an alkyl group, a hydroxy group, an alkoxy group, an amino group, an acylamino group, an alkoxycarbonylamino group or an ureido group, more preferably a group selected from a hydrogen atom, a halogen atom, an alkyl group, an amino group, an acylamino group, an alkoxycarbonylamino group or an ureido group, still more preferably a group selected from a hydrogen atom, an amino group, an acylamino group, an alkoxycarbonylamino group or a ureido group. It is yet still more preferred that $R^{1b}$ and $R^{3b}$ be a hydrogen atom and $R^{2b}$ be a hydrogen atom or an amino group, and it is particularly preferred that all of $R^{1b}$, $R^{2b}$ and $R^{3b}$ be a hydrogen atom.

Further, preferred modes of $R^{1a}$ in Formula (Ia) are also preferable as $R^{3b}$ in the imidazole-4-carboxamide derivative represented by Formula (Ib).

Specific examples of the imidazole-4-carboxamide derivative represented by Formula (Ib) include the following compounds; however, the present invention is not restricted by these compounds.

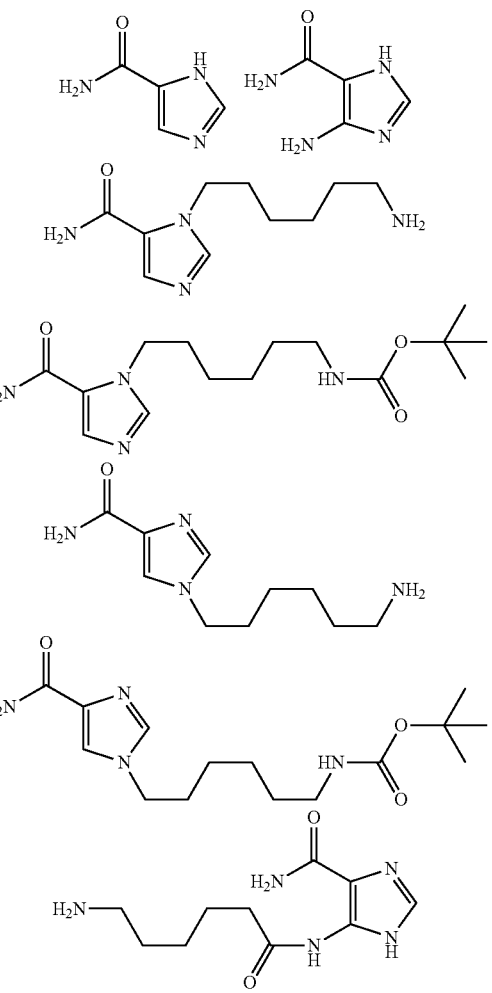

Among those imidazole-4-carboxamide derivatives represented by Formula (Ib), a compound in which all of $R^{1b}$, $R^{2b}$ and $R^{3b}$ are a hydrogen atom, that is, imidazole-4-carboxamide (hereinafter, may be referred to as "ICA"), is a compound including tautomers represented by the following chemical formula. Similarly to the AHX, the ICA is a naturally-occurring compound known to be produced by, for example, a causative fungus of the fairy-ring phenomenon observed in grass growth.

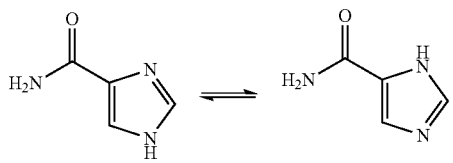 [SMILES: NC(=O)c1c[nH]cn1 ; NC(=O)c1cnc[nH]1]

The ICA may be, as in the case of the AHX, isolated and purified from a culture medium of a causative fungus of the fairy-ring phenomenon by, for example, a conventionally-used method such as extraction or chromatography.

Further, the ICA can also be obtained by amidating ethylimidazole-4-carboxylate in accordance with the method described in Synth. Commun., 17, 1409-1412 (1987).

Furthermore, the ICA can also be obtained by performing denitrification-degradation of the above-described 2-azahypoxanthine (AHX). It is believed that such denitrification-degradation can also occur, for example, in a plant body.

In addition, the imidazole-4-carboxamide derivative represented by Formula (Ib) can be synthesized by a conventionally-used method, for example, using the ICA and a derivative thereof as starting materials.

The staple food crop in the present invention refers to a crop which serves as a major energy source for humans and provides seeds and root vegetables that contain a large amount of carbohydrates, especially starch.

Examples of the staple food crop used in the method of increasing the yield of a staple food crop according to the present invention include cereal crops, tuber crops and pulse crops, and among these, from the standpoints of the staple food crop yield-increasing effect and the demand, the staple food crop is preferably a cereal crop or a tuber crop which is consumed as a staple food in many regions.

From the standpoint of the yield-increasing effect, the cereal crop is preferably a plant belonging to the family Poaceae. Examples thereof include rice (genus *Oryza*), sorghum, maize (genus *Zea*), wheat (genus *Triticum*), barley (genus *Hordeum*), naked barley, rye and oats, and among these, from the standpoints of the staple food crop yield-increasing effect and the demand, the cereal crop is preferably rice, maize or wheat.

Examples of the tuber crops include those plants belonging to the families such as Solanaceae, Convolvulaceae, Asteraceae, Araceae, Dioscoreaceae and Euphorbiaceae. Specific examples thereof include potatoes (family Solanaceae, genus *Solanum*), sweet potatoes (family Convolvulaceae, genus *Ipomoea*), Jerusalem artichokes (family Asteraceae, genus *Helianthus*), eddoes (family Araceae, genus *Colocasia*), konjacs (family Araceae, genus *Amorphophallus*), Chinese yams (family Dioscoreaceae, genus *Dioscorea*), Japanese yams (family Dioscoreaceae, genus *Dioscorea*) and cassayas (family Euphorbiaceae, genus *Manihot*). Among these, from the standpoint of the staple food crop yield-increasing effect, the tuber crop is preferably a potato. The cultivar of the potato is not particularly restricted, and examples thereof include "Danshaku" and May Queen.

The staple food crop in the form of a plant body to be cultured is brought into contact with the a compound represented by Formula (I). Selection of the plant body to be cultured varies depending on the type of the subject staple food crop, and it may be selected based on the normal culture form thereof. The term "plant body to be cultured" used in the present specification refers to an ordinary form of a plant which is exhibited by the plant when grown in a culture site after germination, settled-planting or the like, and the term does not encompass seeds before germination.

For example, when a tuber crop is selected, a root or rhizome thereof may be used as the plant body to be cultured and brought into contact with the compound represented by Formula (I). In sweet potatoes, cassayas and the like, a tuberous root corresponds thereto, in potatoes, a tuber corresponds thereto, and in eddoes, a corm corresponds thereto. These may be generally referred to as "seed tuber". For culturing these roots and rhizomes, a method normally employed to culture a staple food crop may be applied as is, and for example, the roots or rhizomes may be cut into pieces having an appropriate size and then planted in soil.

Further, in the case of a cereal crop, it may be brought into contact with the compound represented by Formula (I) in the form of a plant body after settled-planting. The term "plant body after settled-planting" used herein refers to, for example, in the case of rice, a plant body exhibited by a seedling being settled-planted in a paddy field or one exhibited thereafter, and in the case of maize, a plant body of a germinated seed after being sown or one exhibited thereafter, or a plant body exhibited by a settled-planted seedling or one exhibited thereafter.

In the method of increasing the yield of a staple food crop according to the present invention, the concentration of the compound represented by Formula (I) at which a plant is brought into contact can be selected as appropriate in accordance with the type and growth stage of the plant. Further, the contact method can also be selected arbitrarily. The concentration of the compound represented Formula (I) may generally be not lower than 1 μM, and from the standpoint of the production yield-increasing effect and efficiency, it is preferably from 1 μM to 2 mM, more preferably from 2 μM to 1 mM.

As a culture method, either hydroponic culture or soil culture may be employed, and a conventionally-used culture method may be applied as is in accordance with the type of the staple food crop.

The culture of a tuber crop is generally started by planting a seed tuber in soil. The compound represented by Formula (I) may be added to the culture soil in such an amount that can maintain the above-described concentration range, and is not particularly restricted.

For the culture of a cereal crop, either hydroponic culture or soil culture may be employed. The compound represented by Formula (I) may be appropriately added to a culture liquid or culture soil in such an amount that can maintain the above-described concentration range.

As for the timing of the addition, at a certain time after the start of the culture of a seedling or plant body to be cultured, it may be brought into contact with a prescribed concentration of the compound represented by Formula (I). From the standpoint of making sure to attain a yield-increasing effect, the contact is preferably performed at the initial stage of the culture.

In the case of a tuber crop such as potato, the culture period can be divided into a rooting stage, sprouting stage, germination stage and stage after anthesis and before harvest. The contact with the compound represented by the above-described Formula (I) may be performed in any of these stages; however, from the standpoint of making sure to attain a yield-increasing effect, it is preferred that the contact be performed in the rooting stage which corresponds to the initial stage of the culture.

In the case of a cereal crop such as rice, the culture period can be generally divided into a vegetative stage which is before seedling starts to form panicles; heading stage up until the completion of the panicle formation; and a reproductive stage consisting of an anthesis period and ripening period. The contact with the compound represented by Formula (I) may be performed in any of these stages; however, from the standpoint of making sure to attain a yield-increasing effect, it is preferred that the contact be performed in the period between germination and seedling and/or the vegetative stage.

In cases where the compound represented by Formula (I) is added at the initial stage of the culture, from the standpoint of allowing the germinated or settled-planted plant body to adopt to the culture site, a period of non-contact with the compound represented by Formula (I) may also be provided after the start of the culture. Although the timing of the addition of the compound represented by Formula (I) varies depending on the type of the staple food crop, weather and cultivar; from the standpoint of making sure to attain a staple food crop yield-increasing effect, in the case of a cereal crop, the addition may be performed generally one week after settled-planting or later, preferably two weeks after settled-planting or later, and in the case of a tuber crop such as potato, the addition can be performed 5 days after rooting or later, preferably one week after rooting or later.

The period of the addition is not particularly restricted, and the addition may be performed during the entire period before harvest. Here, as long as the effects of the present invention can be attained, a period of non-contact with the compound represented by Formula (I) may also be provided in the period before harvest.

In the present invention, when the compound represented by Formula (I) is used, it may be used together with a known formulation additive(s). The compound represented by Formula (I) may be used in an arbitrary formulation form. Examples of the known formulation additives include excipients, emulsifying agents and wetting agents. The compound represented by Formula (I) may be in any form, and for example, it may be provided in the form of an emulsion, liquid formulation, oil solution, aqueous solution, wettable powder, flowable, dust formulation, microgranule, granule, aerosol, paste or the like.

In the present invention, an increase in the yield of a staple food crop may be any increase in the yield per plant, and it means an increase in either of the size and number of grains as edible part of the staple food crop. Specifically, in the case of rice, the increase in the yield is, for example, an increase in the weight or number of rice grains, and in the case of a tuber crop, it means an increase in either of the size and number of roots and/or rhizomes as edible organ.

In particular, in the case of a Poaceae plant, the grain weight is increased by bringing the plant into contact with the compound represented by Formula (I) in hydroponic culture, while the number of grains is increased by bringing the plant into contact with the compound represented by Formula (I) in soil culture. As a result, in the case of a Poaceae plant, the yield can be increased regardless of the type of the culture method.

The disclosures of Japanese Patent Application No. 2009-173724 and Japanese Patent Application No. 2009-267916 are hereby incorporated by reference in their entirety.

All of the literatures, patent applications and technical standards described in the present specification are hereby incorporated by reference to the same extent as in cases where each literature, patent application or technical standard is concretely and individually described to be incorporated by reference.

EXAMPLES

The present invention will now be described concretely by way of examples thereof; however, the present invention is not restricted to these examples.

Synthesis Example 1

Synthesis of AHX

AHX was synthesized by diazotizing 5-aminoimidazole-4-carboxamide and then cyclizing the resultant in accordance with the method described in Magn. Reson. Chem., 40, 300-302 (2002).

Synthesis Example 2

The AHX obtained in the above was allowed to react with 6-(Boc-amino)hexylbromide in anhydrous dimethylsulfoxide at 50° C. to obtain the following Example Compounds (1) and (2).

Further, the thus obtained Example Compounds (1) and (2) were treated with trifluoroacetate (TFA) to obtain the following Example Compounds (3) and (4), respectively.

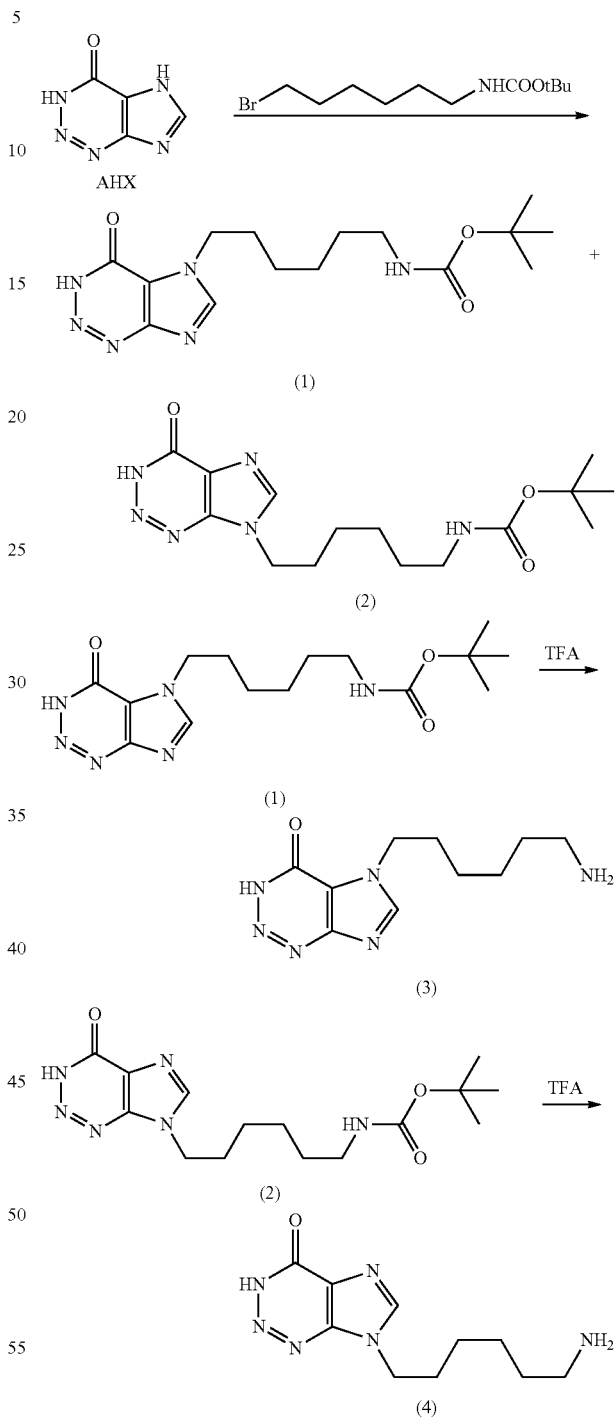

Synthesis Example 3

ICA was synthesized by treating ethylimidazole-4-carboxylate in an aqueous ammonia solution at 100° C. for 4 days in accordance with the method described in Synth. Commun., 17, 1409-1412 (1987).

Example 1

Yield-Increasing Effect in Hydroponic Culture of Rice

Rice (cultivar: "Nipponbare") was used in the test. Seeds thereof were sown in a nursery box, and after 20 days of cultivation, the resulting rice seedlings were transplanted one by one to a pot (1/5000-a) and cultivated for 1 week with tap water.

After the cultivation with tap water, the thus obtained rice plants were cultured in a culture medium added with the AHX (50 μM), which was synthesized in the above, in an outdoor environment over a period of 97 days starting in July.

As the culture medium, a medium containing 0.365 mM of $(NH_4)_2SO_4$, 0.091 mM of $K_2SO_4$, 0.547 mM of $MgSO_4 \cdot 7H_2O$, 0.183 mM of $KNO_3$, 0.365 mM of $Ca(NO_3)_2 \cdot 4H_2O$, 0.182 mM of $KH_2PO_4$, 0.02 mM of Fe-EDTA and 0.002 mM of $Na_2SiO_3$ at pH5.3 was employed.

During the periods from the 8th day to the 32nd day and the period from the 73rd day to the 97th day after the transplantation, the culture was carried out in a medium having a half concentration of the undiluted culture medium, and during the period from the 33rd day to the 72nd day, the undiluted culture medium was used.

Water and nutrients were supplied once every 3 days. As the medium used for the addition, the culture medium for the AHX-treated section and the culture medium for the control section were respectively used in the AHX-treated section and the control section. It is noted here, however, that the culture medium was replaced once a week in the case of hydroponic culture.

The cereal crops obtained by the culture were dried for 2 weeks and the following items were measured: brown rice mass; water content, carbon content and nitrogen content of brown rice; size and number of brown rice (per plant); leaf length; culm length; panicle length; number of panicles; tiller number; and mass of the above-ground and underground parts. Here, the size of brown rice means the mass per grain determined from the brown rice mass (g/100 brown rice grains) and the number of brown rice refers to a value obtained by dividing the brown rice weight (g/plant) by the brown rice weight (g/100 brown rice grains) (number of plants n=6).

The results are shown in Table 1. In Table 1, the symbol "*" indicates that there was a significant difference in t-test at 5% level.

TABLE 1

|  | Control | AHX |
|---|---|---|
| Seed yield | | |
| Brown rice weight (g/plant) | 32.6 | 34.6 * |
| Brown rice weight (g/100 brown rice grains) | 2.12 | 2.24 * |
| Water content (%) | 13.3 | 13.2 |
| Total carbon content (mg/g) | 435 | 429 |
| Total nitrogen content (mg/g) | 16.5 | 16.3 |
| Brown rice size (mg) | 21.2 | 22.4 |
| Number of brown rice (/plant) | 1537 | 1544 |
| Plant size | | |
| Leaf length (cm) | 66.9 | 72.2 * |
| Panicle length (cm) | 19.8 | 21.4 * |
| Culm length (cm) | 60.8 | 60.7 |
| Number of panicles (/plant) | 26.5 | 30.8 * |
| Tiller number (/plant) | 24.5 | 25.1 |
| Mass of the above-ground part (g/plant) | 88.9 | 103 * |
| Mass of underground part (g/plant) | 8.32 | 8.56 |

As shown in Table 1, in the case of hydroponic culture, the brown rice weight per plant was increased by about 6%. Further, the brown rice size and the total brown rice weight increased, and the numbers of brown rice grains were thought to be about the same. Meanwhile, there was no significant difference in the mass of the underground part. From these results, it is suggested that the AHX contributes to increase the size and mass of brown rice, which are important factors for the yield of the staple food crop, not to the growth of the whole plant.

Therefore, in hydroponic culture of a Poaceae plant, by using the compound represented by Formula (I), an increase in the yield based on an increase in the grain size can be expected.

Example 2

Yield-Increasing Effect in Soil Culture of Rice 1

Soil culture was carried out for 97 days starting in July in the same manner as in Example 1, except that seedlings of rice (Nipponbare) were transplanted one by one to a soil (in 1/5000-a pot) which contains a fertilizer containing N (1,440 mg), $P_2O_5$ (12 mg), $K_2O$ (760 mg) and CaO (806 mg).

Water and nutrients were supplied once a day. As the medium used for the addition, the culture medium for the AHX (50 μM)-treated section and the culture medium for the control section were respectively used in the AHX (50 μM)-treated section and the control section. It is noted here that, unlike the case of hydroponic culture, the culture medium was not replaced.

The cereal crops obtained by the soil culture were dried for 2 weeks and the following items were measured in the same manner as in Example 1: brown rice mass; water content, carbon content and nitrogen content of brown rice; size and number of brown rice (per plant); leaf length; culm length; panicle length; number of panicles; tiller number; and mass of the above-ground part (n=7).

The results are shown in Table 2. In Table 2, the symbol "*" indicates that there was a significant difference in t-test at 5% level.

TABLE 2

|  | Control | AHX |
|---|---|---|
| Seed yield | | |
| Brown rice weight (g/plant) | 38.6 | 42.5 * |
| Brown rice weight (g/100 brown rice grains) | 2.29 | 2.28 |
| Water content (%) | 13.9 | 14.0 |
| Total carbon content (mg/g) | 429 | 421 |
| Total nitrogen content (mg/g) | 12.2 | 12.3 |
| Brown rice size (mg) | 22.9 | 22.8 |
| Number of brown rice (/plant) | 1685 | 1864 |
| Plant size | | |
| Leaf length (cm) | 77.5 | 76.5 |
| Panicle length (cm) | 20.2 | 21.1 |
| Culm length (cm) | 69.8 | 70.0 |

TABLE 2-continued

|  | Control | AHX |
|---|---|---|
| Number of panicles (/plant) | 22.8 | 24.5 |
| Tiller number (/plant) | 24.5 | 26.2 |
| Mass of the above-ground part (g/plant) | 112 | 122 * |

As shown in Table 2, in the case of soil culture, the brown rice weight per plant was increased by about 10%. Since the sizes of each brown rice were almost the same, the increase in the total brown rice weight was thought to be attributed to the increase in the number of brown rice. Meanwhile, as the whole rice plant, there was no significant difference in the leaf length and the number of panicles. From these results, it is suggested that the AHX contributes to increase the number of brown rice, which is an important factor for the yield of the staple food crop, not to the growth of the whole plant body.

Therefore, in soil culture of a Poaceae plant, by using the compound represented by Formula (I), an increase in the yield based on an increase in the number of grains can be expected.

Example 3

Yield-Increasing Effect in Soil Culture of Rice 2

Soil culture was carried out from Jun. 10, 2009 to Sep. 29, 2009 in the same manner as in Example 1, except that seedlings of rice (Nipponbare) obtained by a 30-day cultivation were transplanted one by one to a soil (in 1/5000-a pot) which contains a fertilizer containing N (1,440 mg), $P_2O_5$ (12 mg), $K_2O$ (760 mg) and CaO (806 mg).

Water and nutrients were supplied once a day. As the medium used for the addition, the culture medium for the AHX (5 μM)-treated section, the culture medium for the ICA (2 μM)-treated section and the culture medium the control section were respectively used in the AHX (5 μM)-treated section, the ICA (2 μM)-treated section and the control section. It is noted here that, unlike the case of hydroponic culture, the culture medium was not replaced.

The cereal crops obtained by the soil culture were dried for 2 weeks and the following items were measured: brown rice mass; water content of brown rice; size and number of brown rice (per plant); panicle length; culm length; number of panicles; and mass of the above-ground part (n=6).

The results are shown in Table 3. In Table 3, the symbol "*" indicates that there was a significant difference in t-test at 5% level.

TABLE 3

|  | Control | AHX(5 μM) | ICA(2 μM) |
|---|---|---|---|
| Seed yield |  |  |  |
| Brown rice weight (g/plant) | 36.9 | 46.3 * | 46.5 * |
| Brown rice weight (g/100 brown rice grains) | 2.19 | 2.22 | 2.21 |
| Water content (%) | 11.8 | 11.8 | 11.8 |
| Brown rice size (mg) | 21.9 | 22.2 | 22.1 |
| Number of brown rice (/plant) | 1684 | 2086 | 2104 |
| Plant size |  |  |  |
| Panicle length (cm) | 20.7 | 20.8 | 22.1 |
| Culm length (cm) | 84.6 | 89.8 | 87.2 |
| Number of panicles (/plant) | 27.3 | 30.8 | 30.5 |
| Mass of the above-ground part (g/plant) | 134 | 150 | 152 |

As shown in Table 3, when the AHX was used in an amount of 5 μM, the brown rice weight per plant was increased by about 25%. Further, also when the ICA was used in an amount of 2 μM, as in case of the AHX, the grain weight per plant was increased by about 26%.

Since the sizes of each brown rice were almost the same in both cases of the AHX and ICA, the increase in the total brown rice weight was thought to be attributed to the increase in the number of brown rice. Meanwhile, as the whole rice plant, there was no significant difference in the leaf length and the number of panicles. From these results, it is suggested that the AHX and ICA contribute to increase the number of brown rice, which is an important factor for the yield of the staple food crop, not to the growth of the whole plant body.

Therefore, in soil culture of a Poaceae plant, by using the compound represented by Formula (I), an increase in the yield based on an increase in the number of grains can be expected.

Example 4

Yield-Increasing Effect in Soil Culture of Rice 3

Rice (cultivar: "Nipponbare") was used in the test. Seeds thereof were sown in a nursery box, and after 16 days of cultivation, the resulting rice seedlings were transplanted to a pot (1/5000-a) and hydroponically cultured in a culture medium added with the AHX (1 mM) synthesized in the above for 2 weeks before settled-planting.

As the hydroponic medium, a medium containing 0.365 mM of $(NH_4)_2SO_4$, 0.091 mM of $K_2SO_4$, 0.547 mM of $MgSO_4 \cdot 7H_2O$, 0.183 mM of $KNO_3$, 0.365 mM of $Ca(NO_3)_2 \cdot 4H_2O$, 0.182 mM of $KH_2PO_4$, 0.02 mM of Fe-EDTA and 0.002 mM of $Na_2SiO_3$ at pH5.3 was employed.

After the above-described hydroponic culture, the resulting seedlings were settled-planted in soil (in 1/5000-a pot) which contains a fertilizer containing N (1,440 mg), $P_2O_5$ (12 mg), $K_2O$ (760 mg) and CaO (806 mg). and soil-cultured from Jun. 10, 2009 to Sep. 29, 2009 in the same manner as in Example 1. During the soil culture period, no treatment with AHX was performed, and water and nutrients were supplied once per day. It is noted here that the culture medium was not replaced.

The cereal crops obtained by the soil culture were dried for 2 weeks and the following items were measured: brown rice mass; water content of brown rice; size and number of brown rice (per plant); panicle length; culm length; number of panicles; and mass of the above-ground part (n=6).

The results are shown in Table 4. In Table 4, the symbol "*" indicates that there was a significant difference in t-test at 5% level.

TABLE 4

|  | Control | AHX (1 mM-treatment before planting) |
|---|---|---|
| Seed yield |  |  |
| Brown rice weight (g/plant) | 36.9 | 43.6 * |
| Brown rice weight (g/100 brown rice grains) | 2.19 | 2.15 |
| Water content (%) | 11.8 | 11.6 |
| Brown rice size (mg) | 21.9 | 21.5 |
| Number of brown rice (/plant) | 1684 | 2027 |
| Plant size |  |  |
| Panicle length (cm) | 20.7 | 21.1 |
| Culm length (cm) | 84.6 | 86 |

TABLE 4-continued

|  | Control | AHX (1 mM-treatment before planting) |
|---|---|---|
| Number of panicles (/plant) | 27.3 | 33 |
| Mass of the above-ground part (g/plant) | 134 | 154 * |

As shown in Table 4, by performing the treatment with AHX before planting, the brown rice weight per plant was increased by about 18%. Further, since the sizes of each brown rice were almost the same, the increase in the total brown rice weight was thought to be attributed to the increase in the number of brown rice. Meanwhile, there was no significant difference in the leaf length and the number of panicles.

From these results as well, it is suggested that the compound represented by Formula (I) contributes to increase the number of brown rice, which is an important factor for the yield of the staple food crop.

Therefore, in soil culture of a Poaceae plant, by using the compound represented by Formula (I), an increase in the yield based on an increase in the number of grains can be expected.

Example 5

Yield-Increasing Effect in Potato

A seed potato (cultivar: "Danshaku") was cut into pieces of 30 g to 35 g in weight and they were each allowed to take roots in soil (in 1/2000-a pot) which contains a fertilizer containing N (960 mg), $P_2O_5$ (480 mg), $K_2O$ (640 mg) and MgO (320 mg). After 2-weeks of cultivation with tap water (after an above-ground part appeared), 2.74 mg (20 μmol) of AHX was dissolved in tap water and added to the pot every week. The Danshaku potato was cultured in an outdoor environment over a period of 12 weeks starting in January. The control section was treated with tap water only.

After 12 weeks, the Danshaku potato was harvested to measure the tuber mass (for the whole potato and a group consisting of potatoes having a weight of not less than 20 g that were extracted), the length and mass of the above-ground part and the leaf length (n=5).

The results are shown in Table 5. In Table 5, the symbol "*" indicates that there was a significant difference in t-test at 5% level.

TABLE 5

|  | Control | AHX |
|---|---|---|
| Seed yield |  |  |
| Total mass (g/plant) | 80 | 95 * |
| Total mass (g · potatoes of not less than 20 g/plant) | 60 | 85 * |
| Plant size |  |  |
| Length of the above-ground part (cm) | 21 | 24 |
| Leaf length (cm) | 6.6 | 7 |
| Mass of the above-ground part (g/plant) | 25 | 30 |

As shown in Table 5, in those potatoes that were treated with the AHX for 12 weeks and harvested, the total mass was increased by about 19%. Particularly, when only those potatoes having a weight of not less than 20 g were extracted and compared to the control section, the increase was about 40%. Meanwhile, in terms of the length and mass of the above-ground part, there was no significant difference. From these results, it is suggested that the AHX contributes to increase the tuber mass, which is an important factor for the yield of the staple food crop, not to the growth of the whole plant body.

Therefore, in culture of a tuber crop, by using the compound represented by Formula (I), an increase in the yield based on an increase in the mass can be expected.

Example 6

Yield-Increasing Effect in Wheat

In 1/2000-a pots having crushed gravel in the bottom, 6 kg of a paddy-rice nursery soil was placed and, as a base fertilizer, 5-7-6 (N—P—K) was added in an amount of 4 g. The soil was sufficiently watered and 3 days later, 10 grains of wheat (Nourin 61) were sown in each pot.

The wheat was cultured providing 300 ml of water once a week, and the seedlings were thinned 2 weeks after germination to leave 5 seedlings showing good growth.

In the subsequent two weeks, a total of 6 pots were each treated once a week with AHX (5 μM), AHX (50 μM), AHX (1 mM), ICA (2 μM) or water only (control). Then, after culturing for 9 weeks providing 300 ml of just water once a week, the culture was continued for another 12 weeks by changing the amount of water to 500 ml once a week. It is noted here that, 2 weeks after the change was made in the amount of water, 0.75 g of ammonium sulfate was added to each pot as a panicle fertilizer. Further, the AHX (1 mM) treatment pots were subjected to an additional treatment with AHX (1 mM) for 2 weeks after the addition of the panicle fertilizer.

The culture was carried out from Oct. 26, 2009 to May 12, 2010. After the completion of the culture, drying was performed for two weeks and the total wheat yield (g/5 plants) was measured. The results thereof are shown in Table 6. In Table 6, the symbol "*" indicates that there was a significant difference in t-test at 5% level.

TABLE 6

|  | Control | AHX 5 μM | AHX50 μM | AHX 1 mM | ICA 2 μM |
|---|---|---|---|---|---|
| Seed Yield (g/5 plants) | 44.98 ± 0.72 | 44.66 ± 0.99 | 45.68 ± 0.29 | 46.79 ± 0.48 | 47.99 ± 0.31 * |

According to the results shown in Table 6, also in culture of wheat, by using the compound represented by Formula (I), an increase in the yield based on an increase in the mass can be expected.

INDUSTRIAL APPLICABILITY

The method of increasing the yield of a staple food crop according to the present invention has a high industrial applicability since it is capable of increasing the yield of a staple food crop by bringing the compound represented by Formula (I) into contact with a plant body, excluding seeds, to be cultured.

The invention claimed is:

1. A method of increasing the yield of a staple food crop, the method comprising bringing a compound represented by the following Formula (I) into contact with a plant body, excluding seeds, of a staple food crop to be cultured:

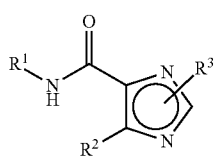

(I)

wherein in Formula (I), R¹ and R² represent a hydrogen atom or are bound together to form an azo group; and R³ represents a hydrogen atom or a monovalent substituent, which is bound to a nitrogen atom of an imidazole ring.

2. The method of increasing the yield of a staple food crop according to claim 1, wherein the compound represented by Formula (I) is 2-azahypoxanthine or imidazole-4-carboxamide.

3. The method of increasing the yield of a staple food crop according to claim 1, wherein the staple food crop is a cereal crop or a tuber crop.

4. The method of increasing the yield of a staple food crop according to claim 1, the method comprising bringing the compound represented by Formula (I) into contact with a plant body of a Poaceae plant to be cultured and performing soil culture.

5. The method of increasing the yield of a staple food crop according to claim 1, the method comprising bringing the compound represented by Formula (I) into contact with a plant body of a Poaceae plant to be cultured and performing hydroponic culture.

6. The method of increasing the yield of a staple food crop according to claim 1, the method comprising bringing the compound represented by Formula (I) into contact with a rhizome or root of a tuber crop to be cultured and performing soil culture, the tuber crop belonging to the family Solanaceae, Convolvulaceae, Asteraceae, Araceae, Dioscoreaceae or Euphorbiaceae.

7. The method of increasing the yield of a staple food crop according to claim 2, wherein the staple food crop is a cereal crop or a tuber crop.

8. The method of increasing the yield of a staple food crop according to claim 2, the method comprising bringing the compound represented by Formula (I) into contact with a plant body of a Poaceae plant to be cultured and performing soil culture.

9. The method of increasing the yield of a staple food crop according to claim 2, the method comprising bringing the compound represented by Formula (I) into contact with a plant body of a Poaceae plant to be cultured and performing hydroponic culture.

10. The method of increasing the yield of a staple food crop according to claim 2, the method comprising bringing the compound represented by Formula (I) into contact with a rhizome or root of a tuber crop to be cultured and performing soil culture, the tuber crop belonging to the family Solanaceae, Convolvulaceae, Asteraceae, Araceae, Dioscoreaceae or Euphorbiaceae.

* * * * *